US006476022B1

(12) United States Patent
Dodd et al.

(10) Patent No.: US 6,476,022 B1
(45) Date of Patent: Nov. 5, 2002

(54) OXATHIEPINO[6,5-B]DIHYDROPYRIDINES, AND RELATED COMPOSITIONS AND METHODS

(75) Inventors: John H. Dodd, Pittstown, NJ (US); James R. Henry, Indianapolis, IN (US); Kenneth C. Rupert, South Orange, NJ (US); James L. Bullington, Hamilton Square, NJ (US); Daniel A. Hall, Somereset, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/603,262

(22) Filed: Jun. 23, 2000

Related U.S. Application Data

(60) Provisional application No. 60/143,354, filed on Jul. 12, 1999.

(51) Int. Cl.$^7$ .................... C07D 497/04; C07D 495/04; A61K 31/4365
(52) U.S. Cl. ................. 514/228.5; 514/234.2; 514/253.04; 514/301; 544/61; 544/127; 544/362; 546/114
(58) Field of Search ............................ 546/114; 544/61, 544/127, 362; 514/301, 228.5, 234.2, 253.04

(56) References Cited

U.S. PATENT DOCUMENTS

| | | | | |
|---|---|---|---|---|
| 4,285,955 A | | 8/1981 | Wehinger et al. ............ 424/266 |
| 4,483,985 A | | 11/1984 | Wehinger et al. ............ 544/131 |
| 4,532,248 A | | 7/1985 | Franckowiak et al. ....... 514/302 |
| 4,845,225 A | | 7/1989 | Schwender et al. .......... 546/114 |
| 4,879,384 A | | 11/1989 | Schwender et al. .......... 546/114 |
| 5,075,440 A | | 12/1991 | Wustrow et al. ............. 540/468 |
| 5,708,177 A | | 1/1998 | Straub ........................ 546/257 |
| 6,291,454 B1 | * | 9/2001 | Bullington et al. ......... 514/227.8 |

FOREIGN PATENT DOCUMENTS

| | | |
|---|---|---|
| CA | 429975 | 9/1945 |
| EP | 241 281 | 7/1994 |
| EP | 462 696 | 8/1995 |
| JP | 58201764 | 11/1983 |
| JP | 61-39760 | 2/1986 |
| JP | 62253161 | 11/1987 |

OTHER PUBLICATIONS

Yedinak, PubMed Abstract (Am. Pharm. NS33(8): 49–64, Aug. 1993).*
Dodd et al., Drug Des. Discov. 1997 15:135–48.
Dodd et al., Drug Des. Discov. 1993, 10–65–75.
Pagani, G.P.A., J. Chem. Soc. Perkin Trans. 2, 1392, (1974).
Biggadike et al., 2000, J. Med Chem. 43:19–21.
Lee et al., 1998, Curr. Opin. Drug Disc. Dev. 1:235–44.
Edema et al. J. Org. Chem. 58: 5624–7, 1993.
Howard et al., J. Amer. Chem. Soc. 82:158–64, 1960).
Eistert et al., (Chem. Ber.100, 1069–1085, 1997).
Mason et al. (J. Chem. Soc. (C) 2171–76, 1967).
E. A. Fehnel (J. Amer. Chem. Soc. 74, 1569–74, 1952).
Leonardi, A. et al.; Asymmetric N–(3,diphenylpropyl)aminoalkyl esters of 4–aryl–2, 6–dimethyl–1, 4–dihydropyridine–3,5–dicarboxylic acids with antihypertensive activity; Eur. J. Med. Chem. 22 (1998); pp. 399–420.

* cited by examiner

Primary Examiner—Deepak R. Rao

(57) ABSTRACT

This invention provides novel oxathiepino[6,5-b] dihydropyridines. These compounds are useful as calcium channel antagonists with cardiovascular, antiasthmatic and antibronchoconstriction activity. Thus, this invention also provides pharmaceutical compositions, as well as methods, for preventing and treating disorders such as hypersensitivity, allergy, asthma, bronchospasm, dysmenorrhea, esophageal spasm, glaucoma, premature labor, urinary tract disorders, gastrointestinal motility disorders and cardiovascular disorders.

40 Claims, No Drawings

OXATHIEPINO[6,5-B]DIHYDROPYRIDINES, AND RELATED COMPOSITIONS AND METHODS

CROSS REFERENCE TO RELATED APPLICATIONS

This application claims the benefit under 335 U.S.C. §119(e) of prior application Ser. No. 60/143,354, filed on Jul. 12, 1999.

FIELD OF THE INVENTION

This invention relates to novel oxathiepino[6,5-b] dihydropyridines useful as calcium channel blockers. These compounds, and related pharmaceutical compositions, are useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

BACKGROUND OF THE INVENTION

Thiacycloalkeno[3,2-b]pyridines are inhibitors of calcium ion uptake into smooth muscle tissue. They act to relax or prevent contraction of the tissue mediated by calcium mechanisms (Dodd et al., Drug Des. Discov. 1997 15:135–48). These compounds are active antihypertensives and bronchodilators.

Thiacycloalkeno[3,2-b]pyridines are also useful for the treatment of cardiovascular disorders, including hypertension, ischemia, angina, congestive heart failure, migraine, myocardial infarction and stroke. Such compounds are also useful for the treatment of other disorders such as hypersensitivity, allergy, asthma, dysmenorrhea, esophageal spasm, gastrointestinal motility disorders, glaucoma, premature labor and urinary tract disorders.

Dodd et al. evaluated a series of thiacycloalkeno[3,2-b] pyridines ranging in sulfone ring size from five to nine membered for calcium antagonist activity. It was found that increasing the sulfone ring size from 5 to 8 members results in an in vitro potency increase of two orders of magnitude. Aromatic substitution patterns which favor tracheal effects over aortic effects were found to be 2-$NO_2$ and 2-Cl, 6-F. The ester side chain which was found to maximize in vivo activity was the N-benzyl-N-methyl aminoethyl moiety (Dodd et al., Drug Des. Discov. 1997, 15:135–48, and Drug Des. Discov. 1993, 10:65–75).

Numerous compounds related to thiacycloalkenopyridines are known, as exemplified by the following publications. U.S. Pat. No. 5,708,177 to Straub discloses a process for the preparation of optically active ortho-substituted 4-aryl-or heteroaryl-1,4-dihydropyridines by oxidation and subsequent reduction from their opposite enantiomers. U.S. Pat. No. 5,075,440 to Wustrow et al. discloses pyrido[2,3-f][1,4]thiazepines and pyrido[3,2-b][1,5]benzothiazepines which are useful as calcium channel antagonists with cardiovascular, antiasthmatic and antibronchoconstriction activity. U.S. Pat. Nos. 4,879,384 and 4,845,225, both to Schwender and Dodd, disclose substituted thiacycloalkeno [3,2-b]pyridines which are also useful as calcium channel antagonists with cardiovascular, antiasthmatic and antibronchoconstrictor activity. U.S. Pat. Nos. 4,285,955 and 4,483,985 disclose acyclic sulfone substitution on simple dihydropyridines which possess calcium channel antagonist activity. U.S. Pat. No. 4,532,248 discloses a broad genus of dihydropyridines, including cyclic sulfones fused to a dihydropyridine nucleus. Cardiotonic activity is disclosed for the entire genus. Finally, 10-Phenyl-2H-thiopyranol[3,2-b]quinolines are disclosed in Pagani, G. P. A., J. Chem. Soc. Perkin Trans. 2, 1392 (1974). However, none of these compounds is a calcium channel antagonist.

"Soft drugs" (also known as "antedrugs") are biologically active drugs which are metabolically inactivated after they achieve their therapeutic role at their designed site of action. The use of soft drugs, instead of their non-inactivatable analogs, avoids unwanted side effects. Soft drugs are known generally (see, for example, Biggadike et al., 2000, J. Med. Chem. 43:19–21; Lee et al., 1998, Curr. Opin. Drug Disc. Dev. 1: 235–44). However, no dihydropyridine soft drugs are known.

SUMMARY OF THE INVENTION

This invention provides novel compounds classified by Formula I as defined hereinbelow, as well as methods for making same. This invention also provides a pharmaceutical composition comprising the instant compound and a pharmaceutically acceptable carrier.

This invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

Finally, this invention provides an apparatus for administering to a subject the instant pharmaceutical composition, comprising a container and the pharmaceutical composition therein, whereby the container has a means for delivering to the subject a therapeutic and/or prophylactic dose of the pharmaceutical composition.

DETAILED DESCRIPTION OF THE INVENTION

This invention provides a compound of Formula I,

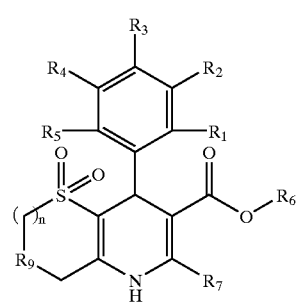

Formula I or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_1$ and $R_2$);
(b) $R_6$ is selected from the group consisting of H, $C_{1-5}$ straight or branched alkyl, aryl, 3-piperidyl, N-substituted 3-piperidyl, N-substituted 2-pyrrolidinyl methylene and substituted alkyl, wherein said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein (i) R' and R" are independently selected from the group consisting of H, $C_{1-8}$ straight or branched alkyl, $C_{3-7}$ cycloalkyl, phenyl, benzyl and phenethyl, or (ii) R' and R" together form a heterocyclic ring selected from the group consisting of piperidino, pyrrolidino, morpholino, thiomorpholino, piperazino, 2-thieno, 3-thieno and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl);

(c) $R_7$ is selected from the group consisting of H, amino, alkyl, aryl, trifluoromethyl, alkoxymethyl, 2-thieno and 3-thieno;

(d) $R_9$ is oxygen or sulfur; and (e) n is an integer from 1 to 4.

In one embodiment of the instant compound $R_6$ is —$(CH_2)_2N(CH_3)CH_2Ph$ or methyl. In a further embodiment, $R_1$, $R_2$, $R_3$, $R_4$ and $R_5$ are independently selected from the group consisting of H, halogen and $NO_2$. In the preferred embodiment, $R_9$ is oxygen.

The following compounds are exemplary of the present invention.

Compound 1: 5H-[1,4]oxathiepino[6,5-b]pyridine-8-carboxylic acid, 2,3,6,9-tetrahydro-7-methyl-9-(3-nitrophenyl), 2-[methyl(phenylmethyl)amino]ethyl ester, 1,1-dioxide.

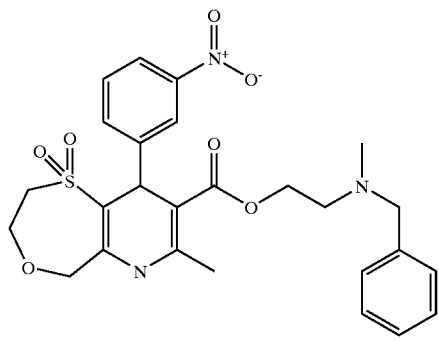

Compound 1

Compound 2: 5H-[1,4]oxathiepino[6,5-b]pyridine-8-carboxylic acid, 9-(2-chlorophenyl)-2,3,6,9-tetrahydro-7-methyl, methyl ester, 1,1-dioxide.

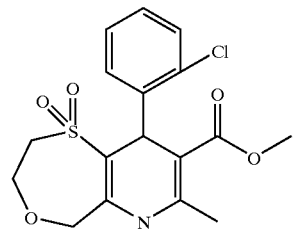

Compound 2

Compound 3: 5H-[1,4]oxathiepino[6,5-b]pyridine-8-carboxylic acid, 9-(2-chlorophenyl)-2,3,6,9-tetrahydro-7-methyl, 2-[methyl(phenylmethyl)amino]ethyl ester, 1,1-dioxide.

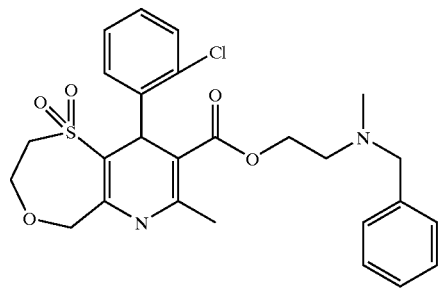

Compound 3

Compound 4: 5H-[1,4]oxathiepino[6,5-b]pyridine-8-carboxylic acid, 2,3,6,9-tetrahydro-7-methyl-9-(3-nitrophenyl), methyl ester, 1,1-dioxide.

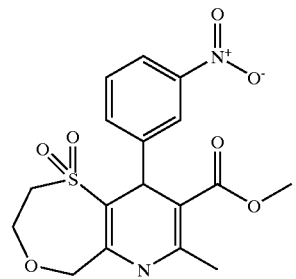

Compound 4

Compound 5: 5H-[1,4]oxathiepino[6,5-b]pyridine-8-carboxylic acid, 2,3,6,9-tetrahydro-7-methyl-9-(2-nitrophenyl), methyl ester, 1,1-dioxide.

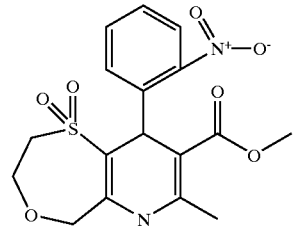

Compound 5

Compound 6: 5H-[1,4]oxathiepino[6,5-b]pyridine-8-carboxylic acid, 9-(3-chlorophenyl)-2,3,6,9-tetrahydro-7-methyl, methyl ester, 1,1-dioxide.

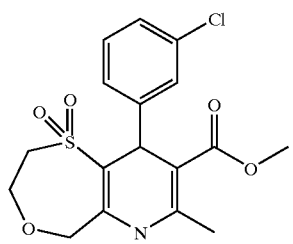

Compound 6

Compound 7: 5H-[1,4]oxathiepino[6,5-b]pyridine-8-carboxylic acid, 9-(3-chlorophenyl)-2,3,6,9-tetrahydro-7-methyl, 2-[methyl(phenylmethyl)amino]ethyl ester, 1,1-dioxide.

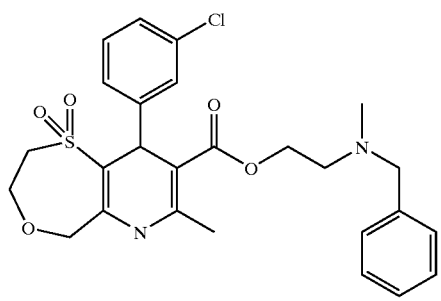

Compound 7

Compound 8: 5H-[1,4]oxathiepino[6,5-b]pyridine-8-carboxylic acid, 2,3,6,9-tetrahydro-7-methyl-9-(2-nitrophenyl), 2-[methyl(phenylmethyl)amino]ethyl ester, 1,1-dioxide.

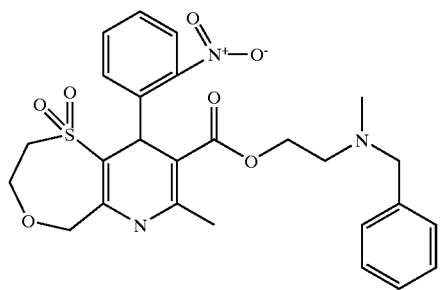

Compound 8

Compound 9: 5H-[1,4]oxathiepino[6,5-b]pyridine-8-carboxylic acid, 9-(2-chloro-6-fluorophenyl)-2,3,6,9-tetrahydro-7-methyl, 2-[methyl(phenylmethyl)amino]ethyl ester, 1,1-dioxide.

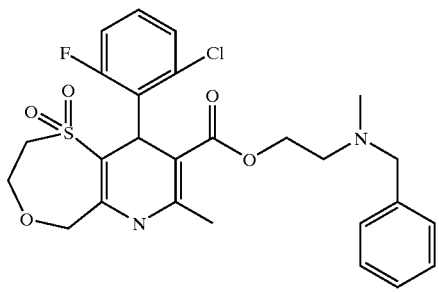

Compound 9

This invention also provides soft drug analogs of the compounds of Formula I. These soft drugs are characterized by a chemically labile moiety bound to the ester group in turn bound to the dihydropyridine ring structure. The soft drugs permit the instant drugs to exert their effect locally, and to subsequently be metabolized in the blood stream, thereby reducing unwanted systemic effects (e.g. low blood pressure). Use of such soft drug analogs permits the administration of greater doses of the claimed dihydropyridine compounds without subjecting the subject to intolerable levels of unwanted systemic effects.

Specifically, this invention provides a compound of Formula II,

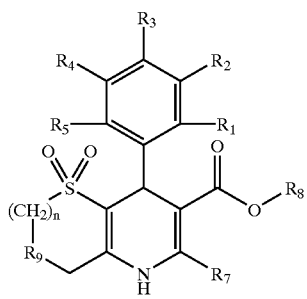

II or a pharmaceutically acceptable salt thereof, wherein
(a) $R_1$, $R_2$, $R_3$, $R_4$, and $R_5$ are independently selected from the group consisting of hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_1$ and $R_2$);
(b) $R_7$ is selected from the group consisting of hydrogen, amino, alkyl, aryl, trifluoromethyl, alkoxymethyl, 2-thieno and 3-thieno;
(c) $R_8$ is selected from the group consisting of -alkyl-OH, alkylamine, lactone, cyclic carbonate, alkyl-substituted cyclic carbonate, aryl-substituted cyclic carbonate, -aryl-C(O)OR', -alkyl-aryl-C(O)OR', -alkyl-OC(O)R', -alkyl-C(O)R', -alkyl-C(O)OR', -alkyl-N(R')C(O)R', and -alkyl-N(R')C(O)OR', wherein
R' and R" are independently selected from the group consisting of hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl); and
(d) $R_9$ is oxygen or sulfur.

Each of the preferred embodiments of the compounds of Formula I set forth above is also contemplated as an embodiment of the compounds of Formula II. In addition, in a preferred embodiment of the compound of Formula II, $R_8$ is selected from -alkyl-OH, lactone, cyclic carbonate, alkyl-substituted cyclic carbonate, aryl-substituted cyclic carbonate, and -alkyl-OC(O)R' wherein R' is as described above.

The following compounds (referred to herein as compound nos. 10–19) are also preferred embodiments of the present invention:

5H-[1,4]oxathiepino[6,5-b]pyridine-8-carboxylic acid, 9-(2,3-dichlorophenyl)-2,3,6,9-tetrahydro-7-methyl-, (5-methyl-2-oxo-1,3-dioxol4-yl)methyl ester, 1,1-dioxide;

5H-[1,4]oxathiepino[6,5-b]pyridine-8-carboxylic acid, 9-(2,
3-dichlorophenyl)-2,3,6,9-tetrahydro-7-methyl-, (2-oxo-
5-phenyl-1,3-dioxol-4-yl)methyl ester, 1,1-dioxide;

5H-[1,4]oxathiepino[6,5-b]pyridine-8-carboxylic acid, 9-(2-
chlorophenyl)-2,3,6,9-tetrahydro-7-methyl-, 2-hydroxy-
ethyl ester, 1,1-dioxide;

5H-[1,4]oxathiepino[6,5-b]pyridine-8-carboxylic acid, 9-(2-
chlorophenyl)-2,3,6,9-tetrahydro-7-methyl-, 2-(2-methyl-
1-oxopropoxy)ethyl ester, 1,1-dioxide;

5H-[1,4]oxathiepino[6,5-b]pyridine-8-carboxylic acid, 9-(2-
chloro-6-fluorophenyl)-2,3,6,9-tetrahydro-7-methyl-,
2-(2-methyl-1-oxopropoxy)ethyl ester, 1,1-dioxide;

5H-[1,4]oxathiepino[6,5-b]pyridine-8-carboxylic acid, 9-(2-
chloro-6-fluorophenyl)-2,3,6,9-tetrahydro-7-methyl-,
2-[(cyclopropylcarbonyl)oxy]ethyl ester, 1,1-dioxide;

5H-[1,4]oxathiepino[6,5-b]pyridine-8-carboxylic acid, 9-(2-
chloro-6-fluorophenyl)-2,3,6,9-tetrahydro-7-methyl-,
2-(acetyloxy)ethyl ester, 1,1-dioxide;

5H-[1,4]oxathiepino[6,5-b]pyridine-8-carboxylic acid, 9-(2-
chloro-6-fluorophenyl)-2,3,6,9-tetrahydro-7-methyl-,
2-[(cyclohexylcarbonyl)oxy]ethyl ester, 1,1-dioxide;

5H-[1,4]oxathiepino[6,5-b]pyridine-8-carboxylic acid, 9-(2-
chloro-6-fluorophenyl)-2,3,6,9-tetrahydro-7-methyl-,
2-(benzoyloxy)ethyl ester, 1,1-dioxide; and 5H-[1,4]oxathiepino[6,5-b]pyridine-8-carboxylic acid, 9-(2-
chlorophenyl)-2,3,6,9-tetrahydro-7-methyl-,
3-(benzoyloxy)propyl ester, 1,1-dioxide.

Unless specified otherwise, the term "alkyl" refers to a straight, branched or cyclic substituent consisting solely of carbon and H with no unsaturation. The term "alkoxy" refers to O-alkyl where alkyl is as defined supra. Illustrative aryl substituents include, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl,,methoxyethyl-phenyl, acetamidophenyl, tolyl, xylyl, dimethyl-carbamylphenyl, —(CH$_2$)$_2$N(CH$_3$)CH$_2$Ph, —CH$_2$CH$_2$—N(Me)—CH$_2$-heteroaryl and the like. The term "halo" means fluoro, chloro, bromo and iodo. The symbol "Ph" refers to phenyl. "Independently" means that when there are more than one substituent, the substitutents may be different.

The compounds of the instant invention are asymmetric in the dihydropyridine ring at the 4-position and thus exist as optical antipodes. As such, all possible optical isomers, antipodes, enantiomers or diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle type column.

As used herein, the phrase "pharmaceutically acceptable salt" means a salt of the free base which possesses the desired pharmacological activity of the free base and which is neither biologically nor otherwise undesirable. These salts may be derived from inorganic or organic acids. Examples of inorganic acids are hydrochloric acid, nitric acid, hydrobromic acid, sulfuric acid, and phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like.

The instant compounds can be prepared using readily available starting materials. The first step of the synthesis as shown hereinafter in Scheme I is well known in the art (Shibata et al., Fuji Photo Film Co., Ltd., Jpn. Kokai Tokkyo Koho, p. 47; JP Patent 62253161, 1987; JP Patent Application 86–39760 (860224); Canadian Patent Application No. 429975, 1988).

This invention also provides a pharmaceutical composition comprising the instant compound and a pharmaceutically acceptable carrier.

Pharmaceutical compositions containing a compound of the present invention as the active ingredient in intimate admixture with a pharmaceutical carrier can be prepared according to conventional pharmaceutical techniques. The carrier may take a wide variety of forms depending on the form of preparation desired for administration, such as systemic administration, including but not limited to intravenous, oral, nasal or parenteral. In preparing the compositions in oral dosage form, any of the usual pharmaceutical carriers may be employed, such as water, glycols, oils, alcohols, flavoring agents, preservatives, coloring agents, syrup and the like in the case of oral liquid preparations (for example, suspensions, elixirs and solutions), or carriers such as starches, sugars, diluents, granulating agents, lubricants, binders, disintegrating agents and the like in the case of oral solid preparations (for example, powders, capsules and tablets).

In a particular embodiment, the compounds of the instant invention are administered by inhalation. For inhalation therapy, the compound may be in a solution useful for administration by metered dose inhalers, or in a form suitable for a dry powder inhaler or insufflator. More particularly, the compounds for use in accordance with the present invention are conveniently delivered in the form of an aerosol spray presentation from a pressurized container, a pack or a nebuliser, for instance, with the use of a suitable propellant, e.g., dichlorodifluoromethane, trichlorofluoromethane, dichlorotetrafluoroethane, carbon dioxide or other suitable gas inside such container. The dosage unit may be determined by providing a valve to deliver a metered amount. Capsules and cartridges made of a pharmaceutically acceptable material such as gelatin for use in an inhaler or insufflator may be formulated containing a powder mix of the compound and a suitable powder base such as lactose or starch.

Because of their ease of administration, tablets and capsules represent an advantageous oral dosage unit form, wherein solid pharmaceutical carriers are employed. If desired, tablets may be sugar-coated or enteric-coated by standard techniques. For parenterals, the carrier will usually comprise sterile water, though other ingredients for solubility or preservative purposes may also be included. Injectable suspensions may also be prepared, wherein appropriate liquid carriers, suspending agents and the like may be employed. The compounds may also be administered in the form of an aerosol.

The instant pharmaceutical compositions will generally contain a per dosage unit (e.g., tablet, capsule, powder, injection, teaspoonful and the like) from about 0.001 to about 100 mg/kg, and preferably from about 0.01 to about 20 mg/kg of the instant compound. Methods are known in the art for determining therapeutically and prophylactically effective doses for the instant pharmaceutical composition. The effective dose for administering the pharmaceutical composition to a human, for example, can be determined mathematically from the results of animal studies.

The compounds of the present invention inhibit the uptake of calcium ions into smooth muscle, and therefore act to relax or prevent calcium ion-mediated contraction of smooth muscle tissue.

Thus, this invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition. By way of example, in a subject suffering from asthma, the subject's airways are constricted due to contraction of airway smooth muscle cells ("SMC's"). Reducing the calcium influx into the SMC's, whose action contributes to the disorder, would be expected to alleviate the disorder.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

In one embodiment, the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder. In the preferred embodiment, the disorder is asthma. The cardiovascular disorder can be, for example, hypertension, ischemia, angina, congestive heart failure, myocardial infarction or stroke.

As used herein, "treating" a disorder means eliminating or otherwise ameliorating the cause and/or effects thereof. "Inhibiting" the onset of a disorder means preventing, delaying or reducing the likelihood of such onset.

The term "subject" includes, without limitation, any animal or artificially modified animal. In the preferred embodiment, the subject is a human.

This invention further provides an apparatus for administering to a subject the instant pharmaceutical composition, comprising a container and the pharmaceutical composition therein, whereby the container has a means for delivering to the subject a therapeutic and/or prophylactic dose of the pharmaceutical composition. In the preferred embodiment, the apparatus is an aerosol spray device for treating and/or preventing asthma via topical respiratory administration.

Finally, as set forth in more detail below, this invention provides a process for preparing the compound of Formula I:

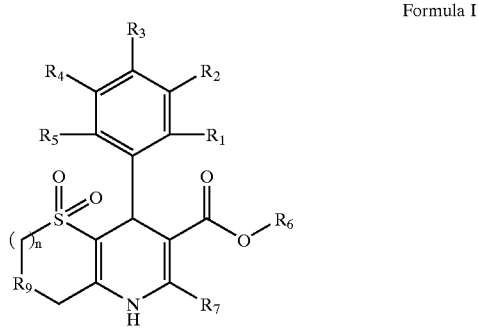

Formula I

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

A. Schemes and Syntheses

Procedures for making dihydropyridines are well documented in the art as shown in Eistert et al. (Chem. Ber. 110, 1069–1085,1977), G. A. Pagani (J. Chem. Soc., Perkin Trans. 2, 1392–7, 1974), Mason et al. (J. Chem. Soc. (C) 2171–76, 1967), E. A. Fehnel (J. Amer. Chem. Soc. 74, 1569–74, 1952), and M. Seiyaku (Japan Patent Application No. 58201764, 1984).

Scheme I shows the preparation of the compounds of Formula I:

Scheme I

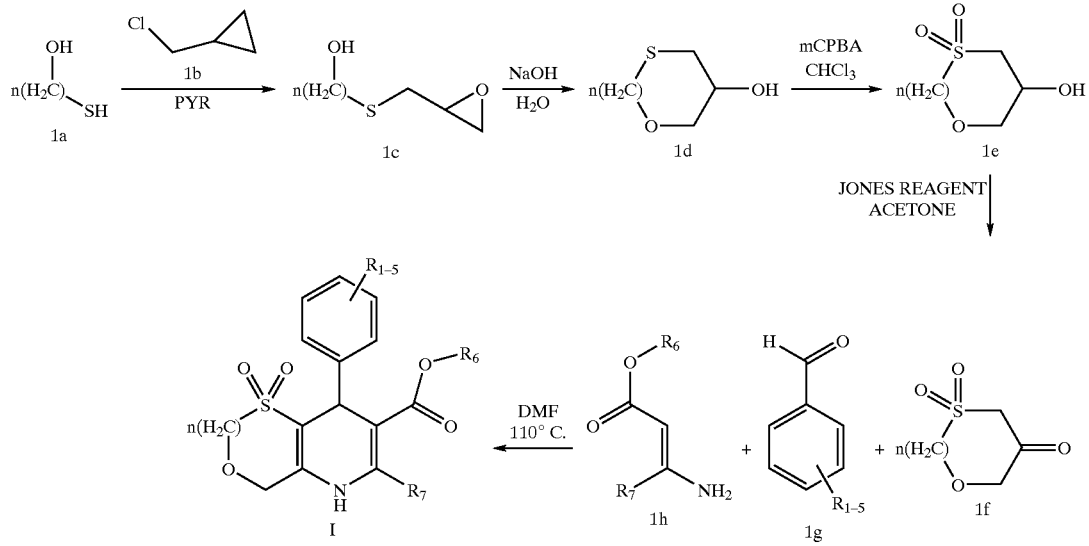

The compounds of Formula II can be made in accordance with Scheme II (wherein compound 2a may be made in steps analogous to those in Scheme I and $R_{1-9}$ are as described above), preferably in the presence of $K_2CO_3$ or $CsCO_3$ in an organic solvent such as dimethylformamide (DMF).

Scheme II

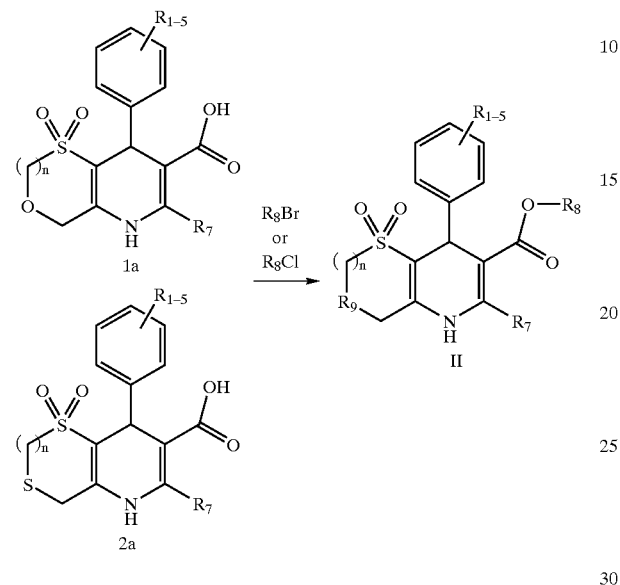

The compounds of Formula 11 may also be made in accordance with Scheme III (wherein compound 3a may be made in steps analogous to those in Scheme 1, and $R_{1-9}$ are as described above), preferably in the presence of formic acid or NaOH (aq), respectively.

Scheme III

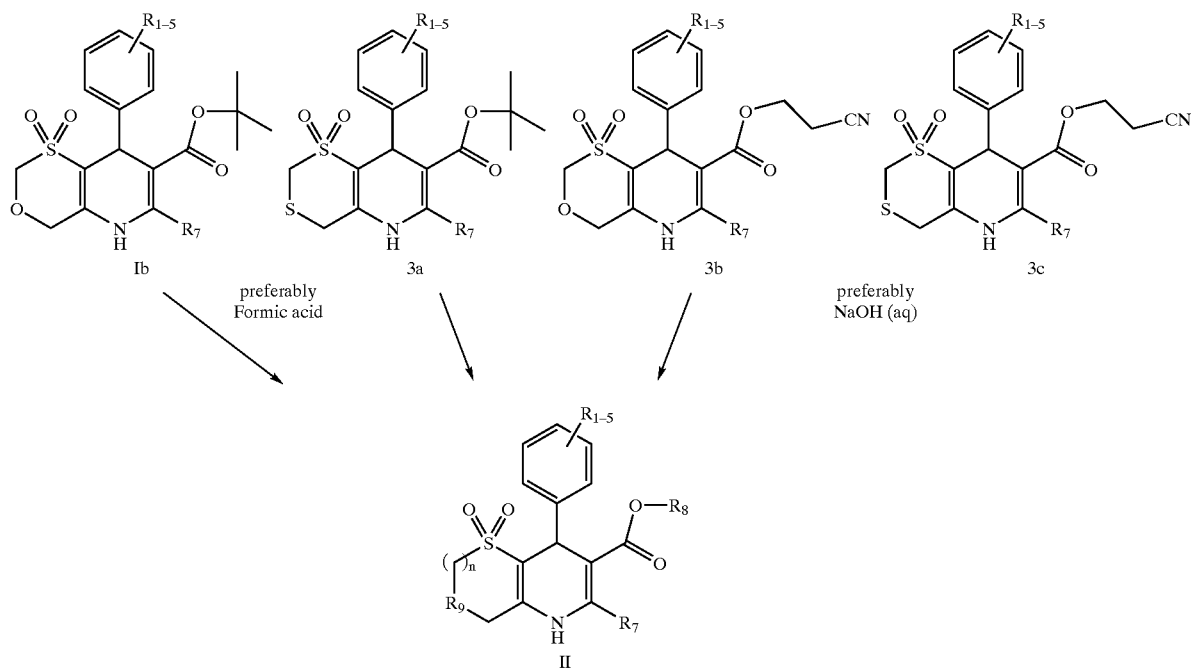

The following examples describe in greater particularity the chemical synthesis of representative compounds of the present invention. The remaining compounds disclosed herein can be prepared similarly in accordance with one or more of these methods. No attempt has been made to optimize the yields obtained in these reactions, and it would be clear to one skilled in the art that variations in reaction times, temperatures, solvents and/or reagents could increase the yields.

EXAMPLE 1

5H-[1,4]Oxathiepino[6,5-b]pyridine-8-carboxylic acid, 9-(2-chlorophenyl)-2,3,6,9-5 tetrahydro-7-methyl, 2-[methyl(phenylmethyl)amino]ethyl ester, 1,1-dioxide

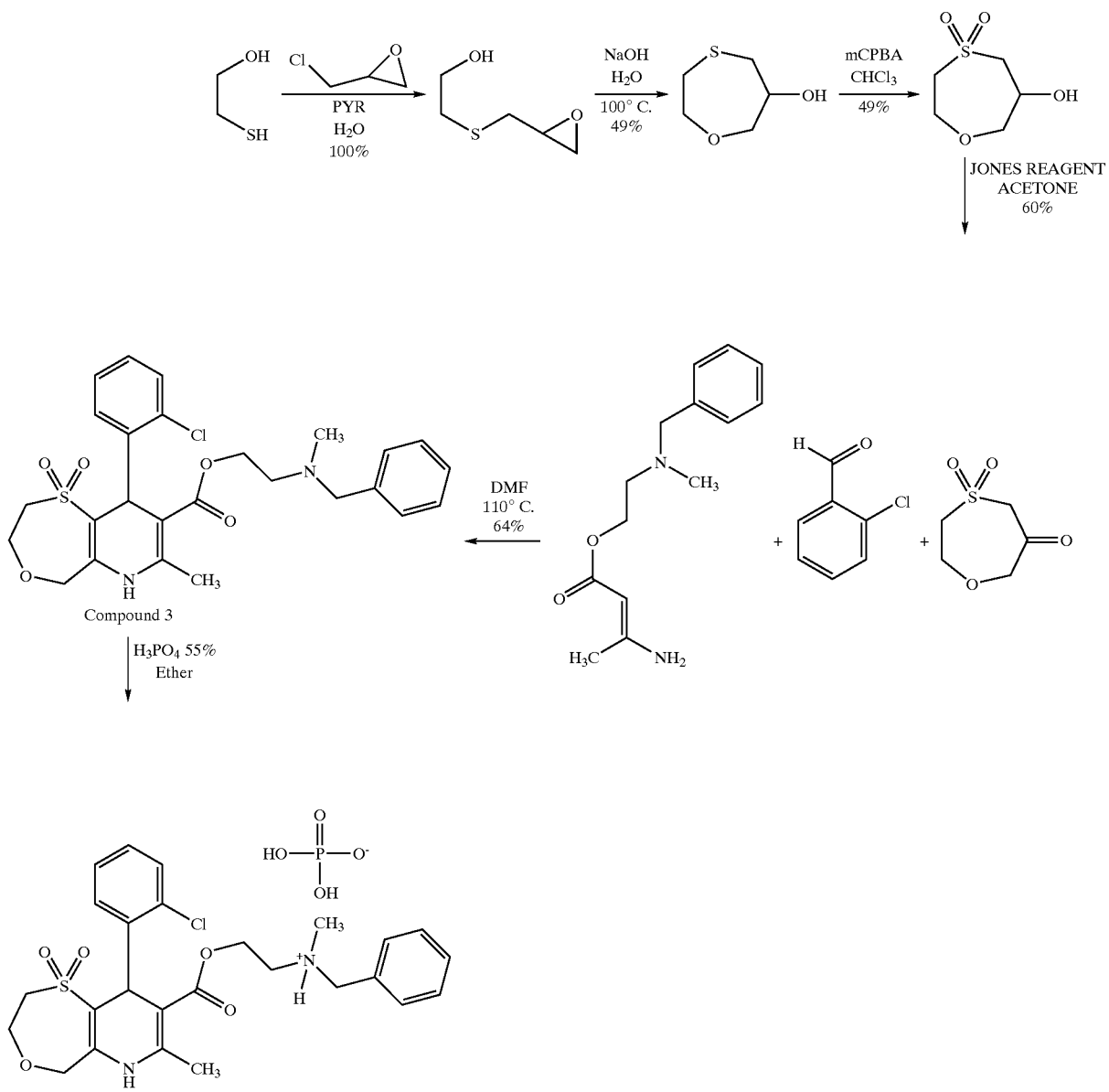

The synthesis of Compound 3, which is shown in Scheme IV above, was performed as follows:

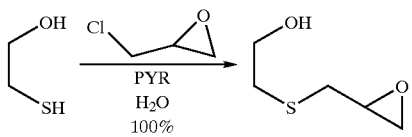

24.95 g (269.7 mmoles) of epichlorohydrin was added dropwise by addition funnel to a solution of 21.07 g (269.7 mmoles) of 2-mercaptoethanol in 100 ml water and 21.33 g (269.7 mmoles) of pyridine at 0° C. After addition was complete, the cooling bath was removed and solution stirred at room temperature for 6 hours. The reaction was then made acidic with 1 N HCL solution and extracted 4×200 ml EtOAc. The organic layers were separated, combined, dried over MgSO$_4$, filtered, and concentrated in vacuo to give 40.8 g of a product of colorless oil (>100% yield). The synthesis of this product (2-[(oxiranylmethyl)thio]ethanol) is described in detail in the literature (*Benzyl alcohol-free rapid processing of silver halide color photographic print paper*, Shibata et al. (Fuji Photo Film Co., Ltd., Japan); Jpn. Kokai Tokkyo Koho, pp.47; JP Patent 62253161,1987; JP Patent Application JP 86–39760, 860224; Canadian Patent Application No.429975, 1988).

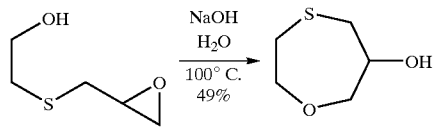

12.16 g (304 mmoles) of sodium hydroxide was dissolved in 120 ml of water. 40.8 g (304 mmoles) of the crude epoxide was added dropwise by addition funnel. The reaction mixture was heated to reflux for 5 hours (during which time the reaction became very dark), cooled to room temperature, made acidic with 6N HCL solution and extracted with 4×400 ml EtOAc. The organic layers were combined, dried over MgSO$_4$, filtered, and concentrated in vacuo to give 20.08g (150 mmoles) of a brown oil that moves slightly faster than starting material on TLC using 1:1 hexane/ethyl acetate to elute.

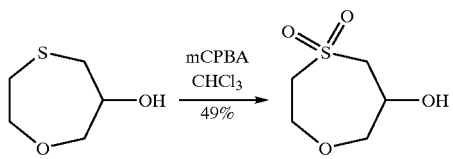

A 1 L 3-neck flask fitted with a thermometer, addition funnel, and air-driven stirrer was charged with 43.5 g (214.1 mmoles) of 85% 3-chloroperoxybenzoic acid and 260 ml CHCl$_3$, and then cooled in an ice bath. 13.06 g (97.32 mmoles) of the crude sulfide in 200 ml CHCl$_3$ was added dropwise by addition funnel over 1 hour. The cooling bath was then removed and the reaction slurry stirred at room temperature for 2 hours. The reaction was then filtered and the filtrate concentrated in vacuo. The residue was treated with ether and decanted. The resultant oil was then treated with warm toluene and decanted to give 9.07 g of a light brown oil. Column chromatography using 1% MeOH in EtOAc afforded 7.9 g (47.53 mmoles) of the sulfone as a light yellow oil.

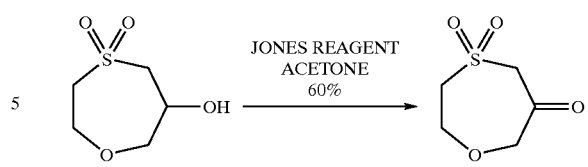

To 7.9 g (47.53 mmoles) of alcohol in 125 ml acetone at 0° was added 20 ml (54 mmoles, 1.1 equivalents) of freshly prepared 2.7M Jones reagent dropwise by addition funnel. The Jones reagent was prepared by carefully dissolving 5.34 g of chromium trioxide in 4.6 ml of concentrated sulfuric acid, and then carefully diluting to 20 ml total volume with water. The cooling bath was removed and the resultant slurry was stirred at room temperature overnight. The reaction slurry was then diluted with 200 ml water and extracted with 4×200 ml EtOAc. The organic layers were separated, combined, washed with 2×200 ml water, dried over MgSO$_4$, filtered and concentrated in vacuo to give a white residue. The residue was triturated with ether/ethyl acetate and filtered to give 4.67 g (28.44 mmoles) of the desired product as a white solid.

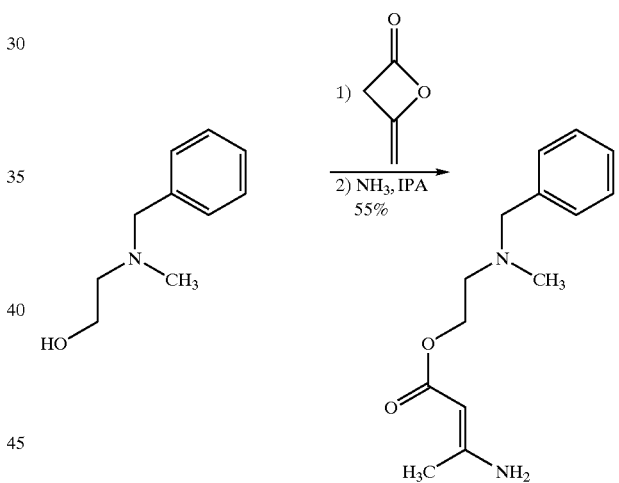

A solution of 25.43 g (153.9 mmoles) of N-benzyl-N-methylethanol amine and 0.2 ml triethylamine was warmed in an oil bath to 60° C. 13.6 g (161.79 mmoles) of diketene was added dropwise by addition funnel, while keeping the reaction temperature between 60–85° C. After addition of diketene was complete, the reaction was stirred another 30 minutes, cooled to room temperature, and then cooled in an ice bath. 20 ml of 2-Propanol was added. Ammonia gas was then bubbled through the reaction mixture for 2 hours. The orange reaction mixture was capped and allowed to stand overnight at 5° C. The reaction mixture was then stirred in an ice bath and 10 ml of heptane was added. A precipitate began to form. After one hour the reaction slurry was filtered and the precipitate was washed with 3×40 ml 10% v/v 2-propanol/heptane to give 21.15 g (85.17 mmoles) of a white solid.

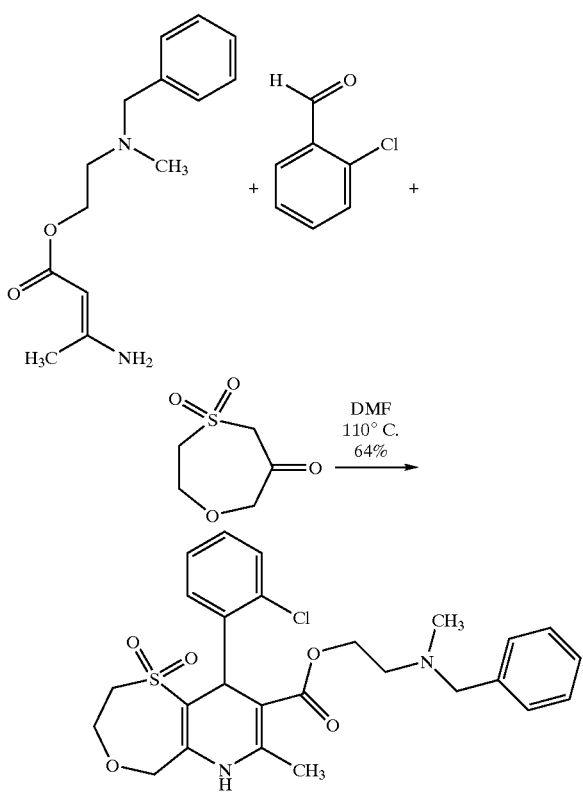

2.4 g (14.62 mmoles) of the cyclic p-ketone sulfone ether, 2.06 g (14.62 mmoles) of 2-chlorobenzaldehyde, and 3.63 g (14.62 mmoles) of 2-(N-benzyl-N-methylamino)ethyl-3-aminocrotonate was heated to 110° C. in 50 ml DMF for 3.5 hours. The reaction was then cooled, diluted with 500 ml EtOAc, washed with 4×200 ml water, 1×100 ml brine, dried over $Na_2SO_4$, filtered and concentrated in vacuo to give a brown oil. Column chromatography using 3:2 EtOAc/hexane afforded 4.87 g (9.42 mmoles) of the desired product (Compound 3) as a yellow foam.

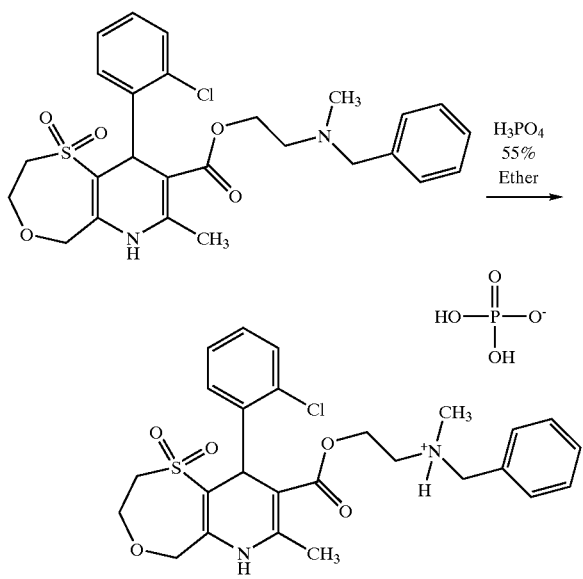

4.87 g (9.42 mmoles) of the dihydropyridine was taken up in 150 ml ether containing a small amount of ethyl acetate. 1.08 g (9.42 mmoles) of 85% orthophosphoric acid in 75 ml ether was added dropwise by addition funnel over 90 minutes. The resultant white slurry was stirred for 4 hours and then filtered. The resultant white solid was washed with excess ether and dried to give 2.68 g (5.18 mmoles) of the phosphate salt.

B. Assays

EXAMPLE 2

Assay for Inhibition of Nitrendipine Binding

Female, New Zealand white rabbits (1–2 kg) are sacrificed by cervical dislocation, and the heart is immediately removed, cleaned and chopped into small pieces. The tissue is homogenized in 5×volume of 0.05M Hepes buffer, pH 7.4. The homogenate is centrifuged at 4000 g for 10 minutes, and the supernatant is re-centrifuged at 42,000 g for 90 minutes. The resulting membrane pellet is resuspended (0.7 ml/g weight) in 0.05M Hepes, pH 7.4 and stored at 70° C. until used. Each tube of the binding assay contains $^3$H-nitrendipine (0.05–0.50 nM), buffer, membranes (0.10 ml ), and test compound in a total volume of 1.0 ml. After 90 minutes at 4° C., the bound nitrendipine is separated from the unbound by filtration on Whatman GF/C filters. After rinsing, the filters are dried and counted in a liquid scintillation counter.

Non-specifically bound $^3$H-nitrendipine (i.e., the amount bound in the presence of excess unlabelled nitrendipine) is subtracted from the total bound to obtain specifically-bound radiolabeled nitrendipine. The amount of specifically-bound nitrendipine in the presence of a test compound is compared to the amount bound in the absence of the compound. A percent displacement (or inhibition) can then be obtained.

EXAMPLE 3

Test for Inhibition of Calcium-Dependent Smooth Muscle Contraction

The trachea and the aorta from dogs sacrificed by excess KCl injection are stored overnight at 4° C. in oxygenated Krebs-Henseleit buffer. Tracheal rings, one cartilage segment wide (5–10 mm), are cut starting from the bronchial end. Rings of aorta tissue of the same width are also prepared. After cutting the cartilage, the trachealis muscle tissue and the aorta tissue are suspended in oxygenated Krebs-Henseleit buffer at 37° C. in a 25 ml tissue bath. After a 60-minute equilibration period, the tissues are challenged with 10 µM carbachol. After 5 minutes, the tissues are rinsed and allowed to rest 50 minutes. The tissues are then challenged with 50 mM KCl and, after 30 minutes, the contractions are quantitated. The tissues are then rinsed and re-equilibrated for 50 minutes. Test compounds are then added for 10 minutes, and the tissue is rechallenged with 50 mM KCl. After 30 minutes, the contraction is recorded and used to determine the % inhibition of control. The percent inhibition of smooth muscle contraction is calculated as follows from response data before and after drug treatment:

% inhibition=100–100×peak response after drug treatment/peak response before drug treatment Table 1 below sets forth the mass spectra data, the inhibition of nitrendipine binding and inhibition of calcium-dependent smooth muscle contraction in terms of percent inhibition for selected compounds of Formula I.

TABLE 1

| Compound Number | Molecular Wt | Amount Submitted | Nitrendipine Binding IC$_{50}$ (nM) | % Yield | Trachea IC$_{50}$ (nM) | Mass Spectroscopy |
|---|---|---|---|---|---|---|
| 1 | 564.0589 | .2355 | 39 | 27.8 | | M + H = 528 |
| 2 | 383.8524 | .1771 | 12 | 46.1 | | M + Na = 406 |
| 3 | 552.51 | .1051 | 129 | 19 | 55 | M + H = 517 |
| 4 | 394.4052 | .1365 | 46 | 34.6 | | M + Na = 417 |
| 5 | 394.4052 | .0448 | 34 | 11.4 | | M + Na = 418 |
| 6 | 383.8524 | .1696 | 21 | 44.2 | | |
| 7 | 553.506 | .3162 | 13 | 57.1 | | M + H = 517 |
| 8 | 564.0589 | .1327 | 86 | 23.5 | | M + H = 528 |
| 9 | 633.0311 | .1667 | — | 13.2 | | M + H = 535 |

Table 2 below sets forth the data for mass spectra and the inhibition of nitrendipine binding for selected compounds of Formula IIa.

TABLE 2

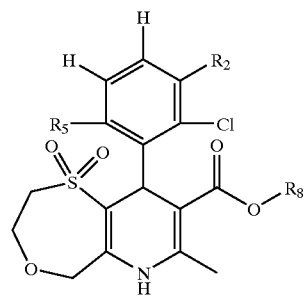

IIa

| Compound Number | R$_2$ | R$_5$ | R$_8$ | Nitrendipine Binding IC$_{50}$ (nM) | Mass Spectroscopy M ± H/M + Na |
|---|---|---|---|---|---|
| 10 | H | F | propyl benzoate | 17 | 558 |
| 11 | H | F | propyl cyclohexanecarboxylate | 96 | 564 |
| 12 | H | F | (CH$_2$)$_2$OC(O)CH$_3$ | 582 | 496 |
| 13 | H | F | propyl cyclopropanecarboxylate | 418 | 522 |
| 14 | H | F | (CH$_2$)$_2$OC(O)CH(CH$_3$)$_2$ | 60 | 524 |
| 15 | H | H | (CH$_2$)$_2$OH | 20000 | 436 |
| 16 | H | H | butyl benzoate | 40 | 554 |
| 17 | H | H | (CH$_2$)$_2$OC(O)CH(CH$_3$)$_2$ | 36 | 506 |
| 18 | Cl | H | (5-phenyl-1,3-dioxol-2-one-4-yl)methyl | 21 | 600 |

TABLE 2-continued

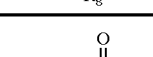

IIa

| Compound Number | $R_2$ | $R_5$ | $R_8$ | Nitrendipine Binding $IC_{50}$ (nM) | Mass Spectroscopy M ± H/M + Na |
|---|---|---|---|---|---|
| 19 | Cl | H | 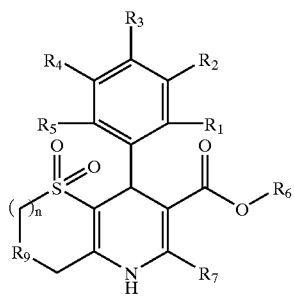 | 18 | 538 |
| 20 | H | F | $(CH_2)_2OH$ | 4362 | 455 |
| 21 | H | H | $(CH_2)_3OH$ | 560 | 426 |

What is claimed is:

1. A compound of Formula I,

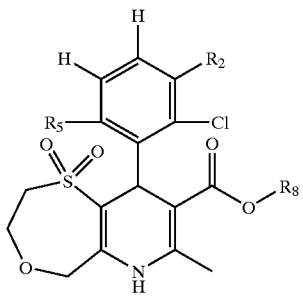

Formula I or a pharmaceutically acceptable salt thereof, wherein (a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, and trifluoromethyl, or an oxadiazole (formed by $R_1$ and $R_2$);

(b) $R_6$ is selected from the group consisting of H, $C_{1-5}$ straight or branched alkyl, aryl, 3-piperidyl, N-substituted 3-piperidyl, N-substituted 2-pyrrolidinyl methylene and substituted alkyl, wherein said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein (i) R' and R" are independently selected from the group consisting of H, $C_{1-8}$ straight or branched alkyl, $C_{3-7}$ cycloalkyl, phenyl, benzyl and phenethyl, or (ii) R' and R" together form a heterocyclic ring selected from the group consisting of piperidino, pyrrolidino, morpholino, thiomorpholino, piperazino, and an N-substituted piperazino ring, said N-substituted piperazino ring being substituted with H, $C_{1-8}$ straight or branched alkyl, benzyl, benzhydryl, phenyl or substituted phenyl (substituted with $NO_2$, halogen, $C_{1-8}$ straight or branched chain alkyl, $C_{1-8}$ alkoxy and/or trifluoromethyl);

(c) $R_7$ is selected from the group consisting of H, amino, alkyl, aryl, trifluoromethyl, alkoxymethyl, 2-thieno and 3-thieno;

(d) $R_9$ is oxygen or sulfur; and (e) n is an integer from 1 to 4.

2. The compound of claim 1, wherein $R_9$ is oxygen.

3. The compound of claim 1, wherein $R_6$ is selected from the group consisting of methyl and —$(CH_2)_2N(CH_3)CH_2Ph$.

4. The compound of claim 1, wherein $R_7$ is methyl.

5. The compound of claim 1, wherein $R_1$, $R_2$, $R_3$, $R_4$, and $R_5$ are independently selected from the group consisting of H, halogen and $NO_2$.

6. The compound of claim 1 which is 5H-[1,4]oxathiepino[6,5-b]pyridine-8-carboxylic acid, 2,3,6,9-tetrahydro-7-methyl-9-(3-nitrophenyl), 2-[methyl(phenylmethyl)amino] ethyl ester, 1,1-dioxide.

7. The compound of claim 1 which is 5H-[1,4]oxathiepino[6,5-b]pyridine-8-carboxylic acid, 9-(2-chlorophenyl)-2,3,6,9-tetrahydro-7-methyl, methyl ester, 1,1-dioxide.

8. The compound of claim 1 which is 5H-[1,4]oxathiepino[6,5-b]pyridine-8-carboxylic acid, 9-(2-chlorophenyl)-2,3,6,9-tetrahydro-7-methyl, 2-[methyl(phenylmethyl)amino] ethyl ester, 1,1-dioxide.

9. The compound of claim 1 which is 5H-[1,4]oxathiepino[6,5-b]pyridine-8-carboxylic acid, 2,3,6,9-tetrahydro-7-methyl-9-(3-nitrophenyl), methyl ester, 1,1-dioxide.

10. The compound of claim 1 which is 5H-[1,4]oxathiepino[6,5-b]pyridine-8-carboxylic acid, 2,3,6,9-tetrahydro-7-methyl-9-(2-nitrophenyl), methyl ester, 1,1-dioxide.

11. The compound of claim 1 which is 5H-[1,4]oxathiepino[6,5-b]pyridine-8-carboxylic acid, 9-(3-chlorophenyl)-2,3,6,9-tetrahydro-7-methyl, methyl ester, 1,1-dioxide.

12. The compound of claim 1 which is 5H-[1,4]oxathiepino[6,5-b]pyridine-8-carboxylic acid, 9-(3-chlorophenyl)-2,3,6,9-tetrahydro-7-methyl, 2-[methyl(phenylmethyl)amino]ethyl ester, 1,1-dioxide.

13. The compound of claim 1 which is 5H-[1,4]oxathiepino[6,5-b]pyridine-8-carboxylic acid, 2,3,6,9-tetrahydro-7-methyl-9-(2-nitrophenyl), 2-[methyl(phenylmethyl)amino]ethyl ester, 1,1-dioxide.

14. The compound of claim 1 which is 5H-[1,4]oxathiepino[6,5-b]pyridine-8-carboxylic acid, 9-(2-chloro-6-fluorophenyl)-2,3,6,9-tetrahydro-7-methyl, 2-[methyl(phenylmethyl)amino]ethyl ester, 1,1-dioxide.

15. The compound of Formula (II), wherein

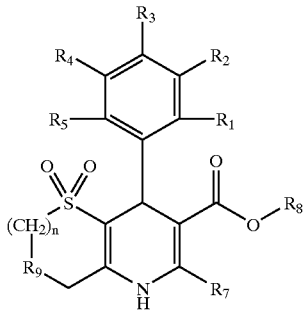

(a) $R_1$, $R_2$, $R_3$, $R_4$ and $R_5$ are independently selected from the group consisting of hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, and trifluoromethyl, or an oxadiazole (formed by $R_1$ and $R_2$);

(b) $R_7$ is selected from the group consisting of H, amino, alkyl, aryl, trifluoromethyl, alkoxymethyl, 2-thieno and 3-thieno;

(c) $R_8$ is selected from the group consisting of -alkyl-OH, alkylamine, lactone, cyclic carbonate, alkyl-substituted cyclic carbonate, aryl-substituted cyclic carbonate, -aryl-C(O)OR', -alkyl-aryl-C(O)OR', -alkyl-OC(O)R', -alkyl-C(O)R', -alkyl-C(O)OR', -alkyl-N(R')C(O)R', and -alkyl-N(R')C(O)OR', wherein R' and R" are independently selected from the group consisting of hydrogen, amino, alkyl, aryl, aryl-fused cycloalkyl and a 5 or 6 membered saturated or unsaturated heterocyclyl having one nitrogen or one nitrogen and either a second nitrogen, a sulfur or an oxygen, the amino, alkyl, aryl, aryl-fused cycloalkyl and heterocyclyl being optionally substituted with halogen, cyano, $NO_2$, lactone, amino, alkylamino, aryl-substituted alkylamino, amido, carbamate, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$; carboalkoxy, alkylthio and/or trifluoromethyl); and (d) $R_9$ is oxygen or sulfur.

16. The compound of claim 15, wherein $R_9$ is oxygen.

17. The compound of claim 15, wherein $R_7$ is methyl, and $R_1$, $R_2$, $R_3$, $R_4$, and $R_5$ are independently selected from hydrogen, halogen, trifluoromethyl and $NO_2$.

18. The compound of claim 15, wherein $R_8$ is selected from -alkyl-OH, lactone, cyclic carbonate, alkyl-substituted cyclic carbonate, aryl-substituted cyclic carbonate and -alkyl-OC(O)R'.

19. The compound of claim 15 which is 5H-[1,4]oxathiepino[6,5-b]pyridine-8-carboxylic acid, 9-(2,3-dichlorophenyl)-2,3,6,9-tetrahydro-7-methyl-, (5-methyl-2-oxo-1,3-dioxol-4-yl)methyl ester, 1,1-dioxide.

20. The compound of claim 15 which is 5H-[1,4]oxathiepino[6,5-b]pyridine-8-carboxylic acid, 9-(2,3-dichlorophenyl)-2,3,6,9-tetrahydro-7-methyl-, (2-oxo-5-phenyl-1,3-dioxol-4-yl)methyl ester, 1,1-dioxide.

21. The compound of claim 15 which is 5H-[1,4]oxathiepino[6,5-b]pyridine-8-carboxylic acid, 9-(2-chlorophenyl)-2,3,6,9-tetrahydro-7-methyl-, 2-hydroxyethyl ester, 1,1-dioxide.

22. The compound of claim 15 which is 5H-[1,4]oxathiepino[6,5-b]pyridine-8-carboxylic acid, 9-(2-chlorophenyl)-2,3,6,9-tetrahydro-7-methyl-, 2-(2-methyl-1-oxopropoxy)ethyl ester, 1,1-dioxide.

23. The compound of claim 15 which is 5H-[1,4]oxathiepino[6,5-b]pyridine-8-carboxylic acid, 9-(2-chloro-6-fluorophenyl)-2,3,6,9-tetrahydro-7-methyl-, 2-(2-methyl-1-oxopropoxy)ethyl ester, 1,1-dioxide.

24. The compound of claim 15 which is 5H-[1,4]oxathiepino[6,5-b]pyridine-8-carboxylic acid, 9-(2-chloro-6-fluorophenyl)-2,3,6,9-tetrahydro-7-methyl-, 2-[(cyclopropylcarbonyl)oxy]ethyl ester, 1,1-dioxide.

25. The compound of claim 15 which is 5H-[1,4]oxathiepino[6,5-b]pyridine-8-carboxylic acid, 9-(2-chloro-6-fluorophenyl)-2,3,6,9-tetrahydro-7-methyl-, 2-(acetyloxy)ethyl ester, 1,1-dioxide.

26. The compound of claim 15 which is 5H-[1,4]oxathiepino[6,5-b]pyridine-8-carboxylic acid, 9-(2-chloro-6-fluorophenyl)-2,3,6,9-tetrahydro-7-methyl-, 2-[(cyclohexylcarbonyl)oxy]ethyl ester, 1,1-dioxide.

27. The compound of claim 15 which is 5H-[1,4]oxathiepino[6,5-b]pyridine-8-carboxylic acid, 9-(2-chloro-6-fluorophenyl)-2,3,6,9-tetrahydro-7-methyl-, 2-(benzoyloxy)ethyl ester, 1,1-dioxide.

28. The compound of claim 15 which is 5H-[1,4]oxathiepino[6,5-b]pyridine-8-carboxylic acid, 9-(2-chlorophenyl)-2,3,6,9-tetrahydro-7-methyl-, 3-(benzoyloxy)propyl ester, 1,1-dioxide.

29. A pharmaceutical composition comprising an effective amount of the compound of claim 1 or 15 and a pharmaceutically acceptable carrier.

30. A method of treating a subject suffering from a disorder whose alleviation is mediated by the reduction of calcium ion influx into cells whose actions contribute to the disorder, which method comprises administering to the subject a therapeutically effective dose of the pharmaceutical composition of claim 29.

31. The method of claim 30, wherein the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder.

32. The method of claim 31, wherein the disorder is asthma.

33. The method of claim 31, wherein the cardiovascular disorder is selected from the group consisting of hypertension, ischemia, angina, congestive heart failure, myocardial infarction and stroke.

34. A method of inhibiting in a subject the onset of a disorder whose alleviation is mediated by the reduction of calcium ion influx into cells whose actions contribute to the disorder, which method comprises administering to the subject a therapeutically effective dose of the pharmaceutical composition of claim 29.

35. The method of claim 34, wherein the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder.

36. The method of claim 35, wherein the disorder is asthma.

37. The method of claim 35, wherein the cardiovascular disorder is selected from the group consisting of hypertension, ischemia, angina, congestive heart failure, myocardial infarction and stroke.

38. The method of claim 34, wherein the subject has normal or low blood pressure.

39. An apparatus for administering to a subject the pharmaceutical composition of claim 29, comprising a container and the pharmaceutical composition therein, wherein the container has a means for delivering a to the subject a therapeutic dose of the pharmaceutical composition.

40. A process for preparing the compound of claim 2, comprising the steps of:

(a) reacting the compound of Formula 1a with the compound of Formula 1b to form the compound of Formula 1c;

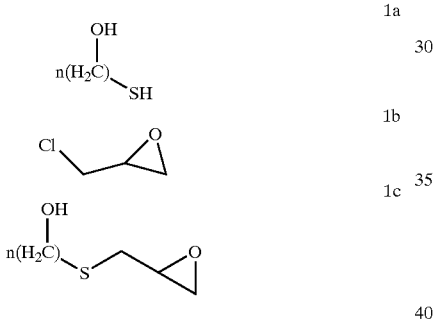

(b) treating the compound of Formula 1c with NaOH to form the compound of Formula 1d;

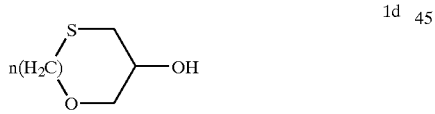

(c) treating the compound of Formula 1d with m-chloroperoxybenzoic acid and $CHCl_3$ to form the compound of Formula 1e;

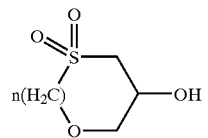

(d) treating the compound of Formula 1e with Jones Reagent and acetone to form the compound of Formula 1f; and

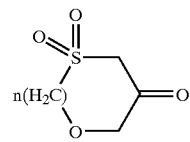

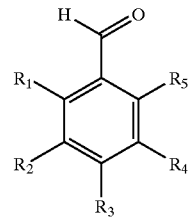

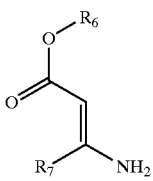

(e) reacting the compound of Formula 1f with the compounds of Formulae 1g and 1h to form the compound of claim 2.

\* \* \* \* \*